(12) United States Patent  
Cermak

(10) Patent No.: US 11,950,804 B2  
(45) Date of Patent: Apr. 9, 2024

(54) PARALLEL PATH PUNCTURE DEVICE GUIDE

(71) Applicant: INNOVACELL AG, Innsbruck (AT)

(72) Inventor: Craig Joseph Cermak, Iowa City, IA (US)

(73) Assignee: INNOVACELL AG, Innsbruck (AT)

( * ) Notice: Subject to any disclaimer, the term of this patent is extended or adjusted under 35 U.S.C. 154(b) by 95 days.

(21) Appl. No.: 17/765,906

(22) PCT Filed: Oct. 2, 2020

(86) PCT No.: PCT/US2020/053988  
§ 371 (c)(1),  
(2) Date: Apr. 1, 2022

(87) PCT Pub. No.: WO2021/067734  
PCT Pub. Date: Apr. 8, 2021

(65) Prior Publication Data  
US 2022/0378466 A1    Dec. 1, 2022

Related U.S. Application Data

(60) Provisional application No. 62/911,057, filed on Oct. 4, 2019.

(51) Int. Cl.  
*A61B 17/34* (2006.01)  
*A61B 8/12* (2006.01)

(52) U.S. Cl.  
CPC ............ *A61B 17/3403* (2013.01); *A61B 8/12* (2013.01); *A61B 2017/3405* (2013.01); *A61B 2017/3413* (2013.01)

(58) Field of Classification Search  
CPC .................. A61B 17/3403; A61B 8/12; A61B 2017/3405; A61B 2017/3413;  
(Continued)

(56) References Cited

U.S. PATENT DOCUMENTS 4,776,346 A * 10/1988 Beraha ............... A61B 10/0241  
    600/567  
4,869,258 A    9/1989 Hetz  
(Continued)

FOREIGN PATENT DOCUMENTS

EP    0 446 645    9/1991  
EP    1 337 183    8/2003  
(Continued)

OTHER PUBLICATIONS

International Search Report and Written Opinion issued in International Application No. PCT/US2020/053988, dated Jan. 25, 2021.  
(Continued)

*Primary Examiner* — Sean D Mattson  
*Assistant Examiner* — Michael Yiming Fang  
(74) *Attorney, Agent, or Firm* — Parker Highlander PLLC

(57) ABSTRACT

A puncture device guide includes a body member configured to fixedly attach to an ultrasound probe, a slide member slidingly received within the body member; and a cradle member slidingly received within the slide member and longitudinally fixed relative to the body member. The cradle member is configured to receive a puncture device therein. Longitudinal movement of the slide member causes radial movement of the cradle member relative to the body member.

12 Claims, 14 Drawing Sheets

(58) Field of Classification Search
CPC ....... A61B 2017/00274; A61B 8/0841; A61M 5/178; A61M 2205/3375; A61M 2209/04; A61M 5/3287
See application file for complete search history.

(56) References Cited

U.S. PATENT DOCUMENTS

| | | | |
|---|---|---|---|
| 4,877,033 A | 10/1989 | Seitz, Jr. | |
| 4,883,059 A | 11/1989 | Stedman et al. | |
| 4,892,520 A | 1/1990 | Gilbaugh | |
| 4,899,756 A * | 2/1990 | Sonek | A61B 8/0841 600/461 |
| 4,900,303 A | 2/1990 | Lemelson | |
| 5,078,144 A | 1/1992 | Sekino et al. | |
| 5,235,987 A | 8/1993 | Wolfe | |
| 5,494,039 A * | 2/1996 | Onik | A61B 17/3403 600/562 |
| 6,309,374 B1 | 10/2001 | Hecker et al. | |
| 8,926,494 B1 | 1/2015 | Cook et al. | |
| 2002/0156376 A1 | 10/2002 | Wang et al. | |
| 2005/0059891 A1 | 3/2005 | Kosaku | |
| 2012/0259221 A1 * | 10/2012 | Sheldon | A61M 25/0105 600/439 |
| 2014/0200445 A1 * | 7/2014 | Boezaart | A61B 8/4209 600/461 |
| 2014/0290666 A1 | 10/2014 | Agee et al. | |
| 2015/0250447 A1 | 9/2015 | Kubota et al. | |
| 2016/0022309 A1 * | 1/2016 | Allaway | A61B 8/12 600/464 |
| 2016/0128719 A1 * | 5/2016 | Cermak | A61B 8/0841 600/461 |
| 2017/0020558 A1 | 1/2017 | Xu et al. | |
| 2019/0223977 A1 * | 7/2019 | Galili | A61M 5/20 |
| 2019/0282262 A1 * | 9/2019 | Bouazza-Marouf | A61B 17/3403 |
| 2020/0214739 A1 * | 7/2020 | Shi | A61B 1/07 |
| 2021/0338267 A1 * | 11/2021 | Allaway | A61B 10/0241 |
| 2022/0096065 A1 * | 3/2022 | Fisher | A61B 17/3476 |
| 2023/0240643 A1 | 8/2023 | Cermak et al. | |

FOREIGN PATENT DOCUMENTS

| | | |
|---|---|---|
| EP | 2 170 440 | 4/2010 |
| FR | 2 895 681 | 7/2007 |
| WO | WO 95/02663 | 1/1995 |
| WO | WO 2006/128718 | 12/2006 |
| WO | WO 2021/067734 | 4/2021 |

OTHER PUBLICATIONS

Frudinger, A. et al. "Skeletal muscle-derived cell implantation for the treatment of sphincter-related faecal incontinence," *Stem Cell Research & Therapy*, 9.233 (2018): 1-20.

International Search Report and Written Opinion issued in International Patent Application No. PCT/EP2021/06686, dated Oct. 5, 2021.

Messner, F. et al., "Myogenic progenitor cell transplantation for muscle regeneration following hindlimb ischemia and reperfusion," *Stem Cell Research & Therapy*, 12.146 (2021): 1-15.

Thurner, M. et al., "Generation of myogenic progenitor cell-derived smooth muscle cells for sphincter regeneration," *Stem Cell Research & Therapy*, 11.233 (2020): 1-17.

* cited by examiner

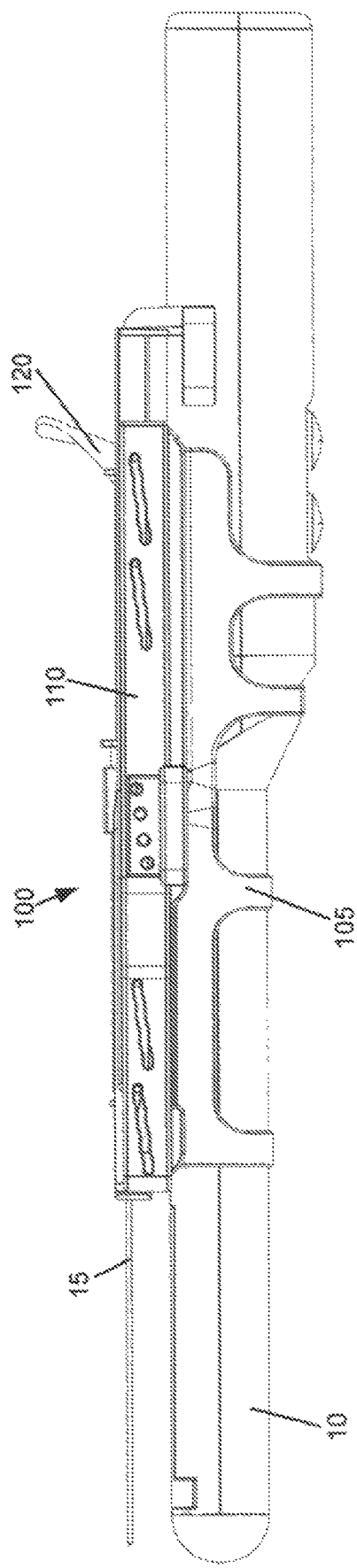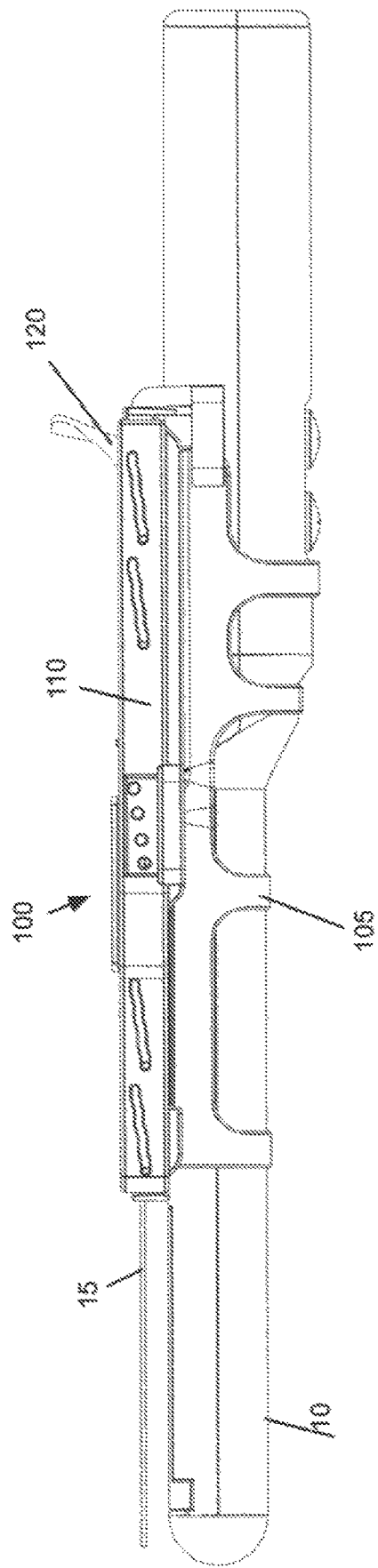

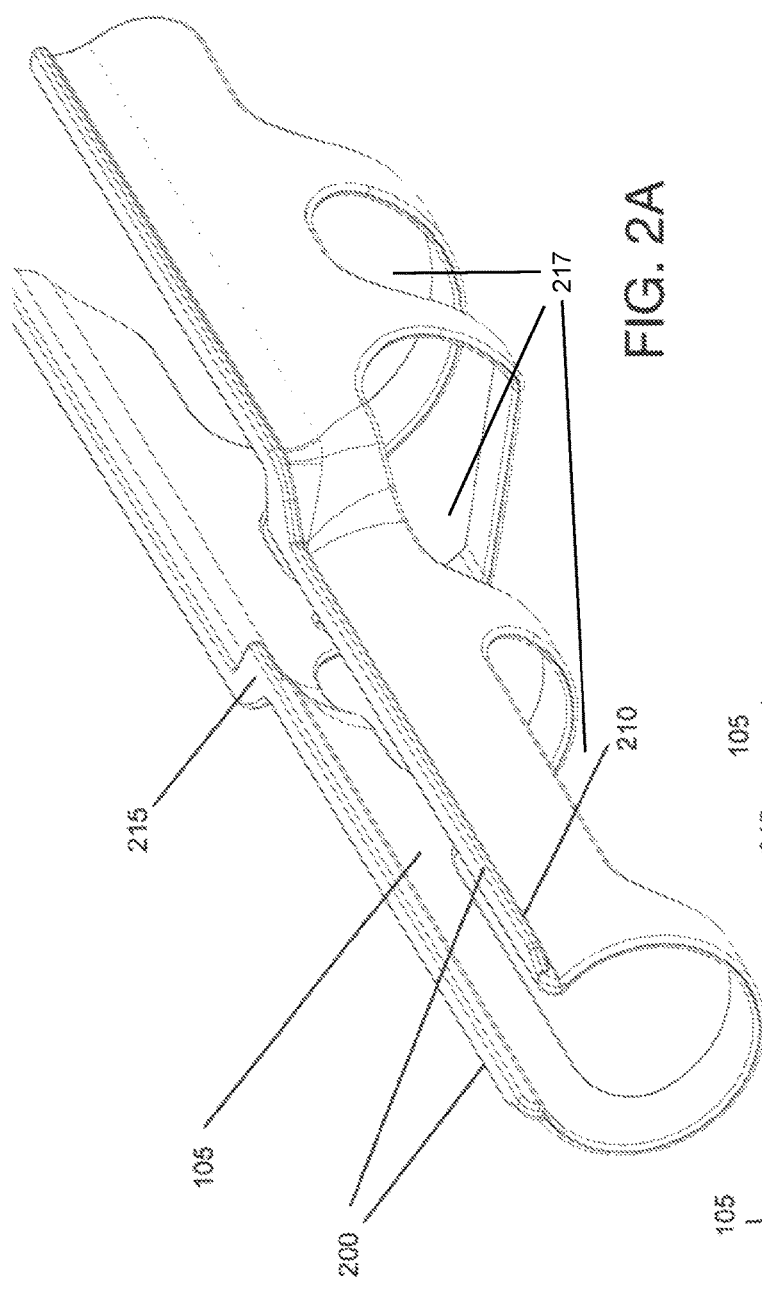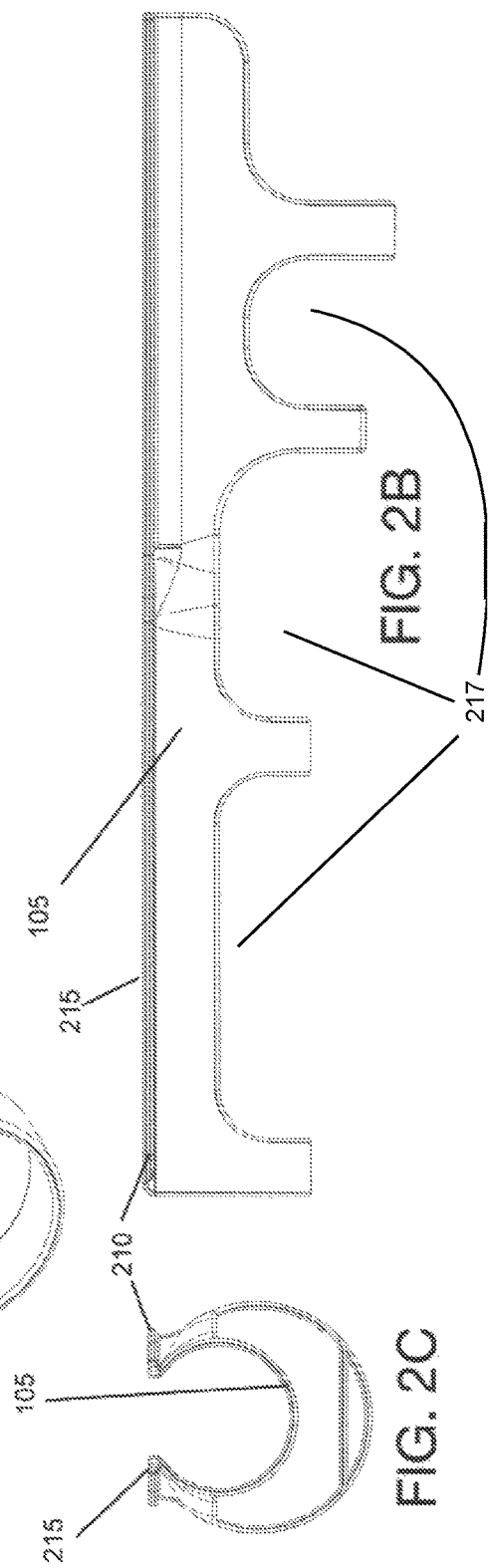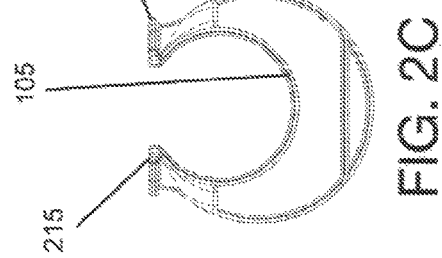

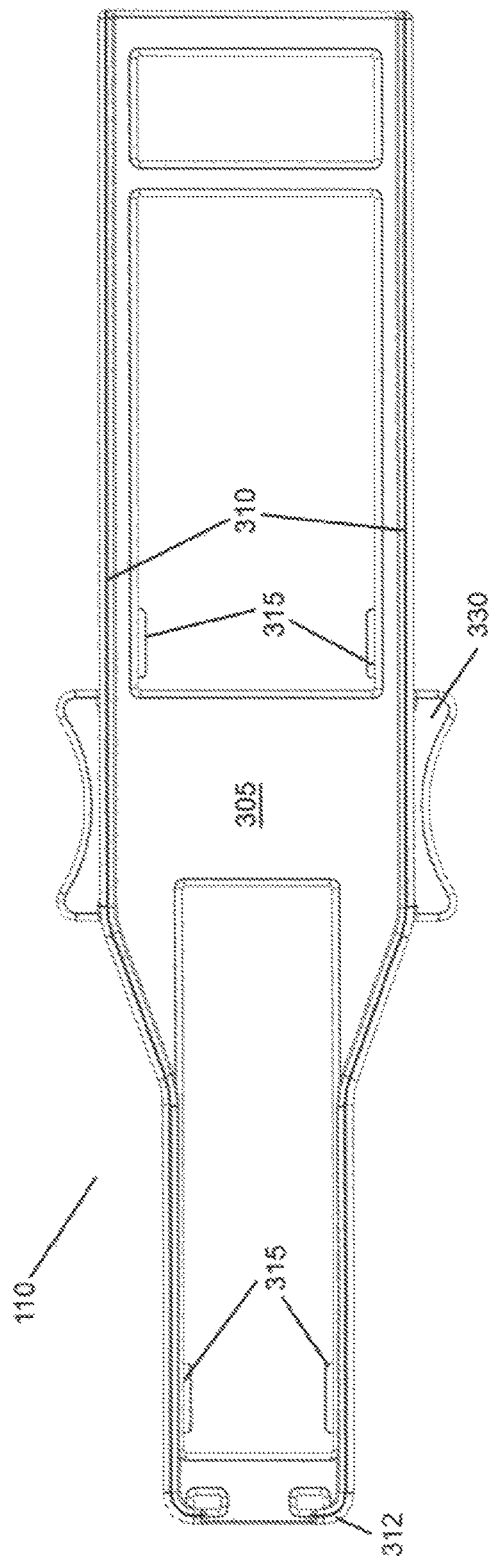
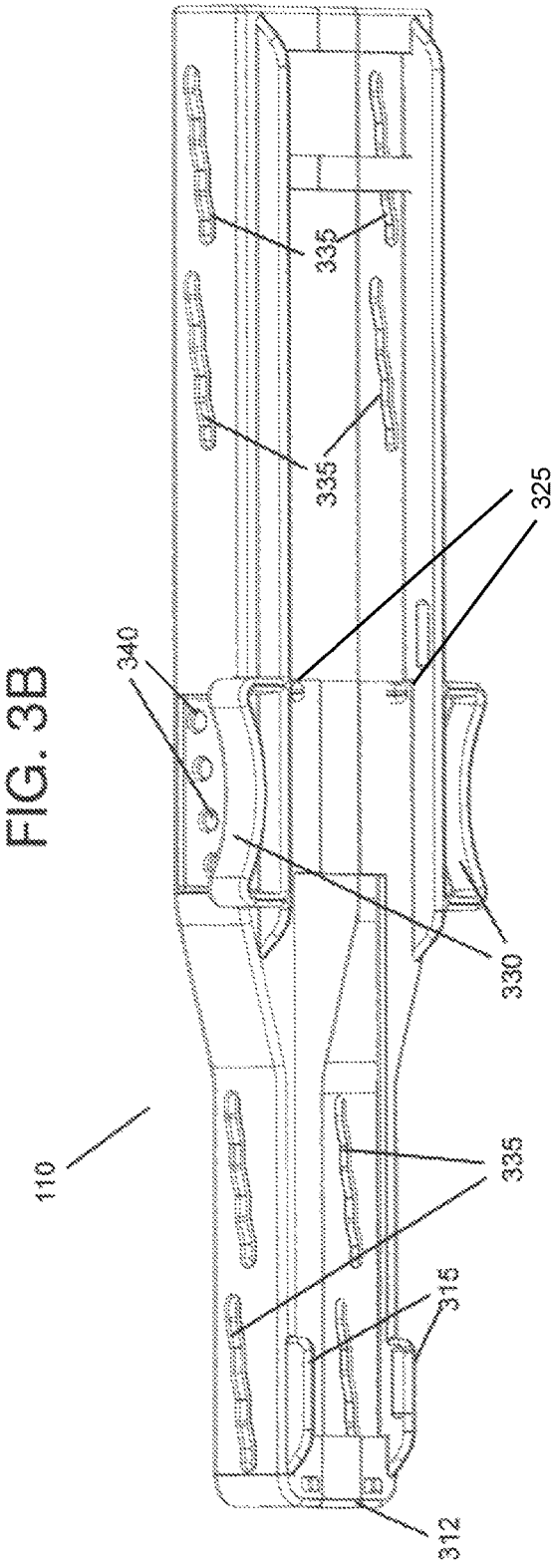
FIG. 3B
FIG. 3C

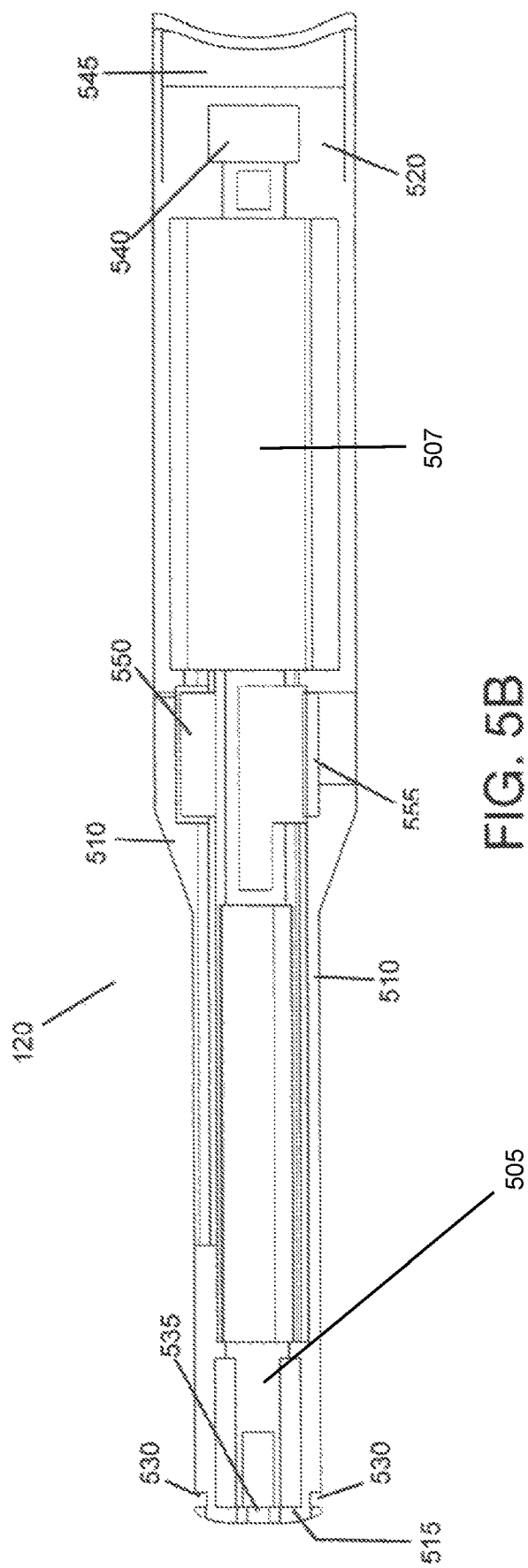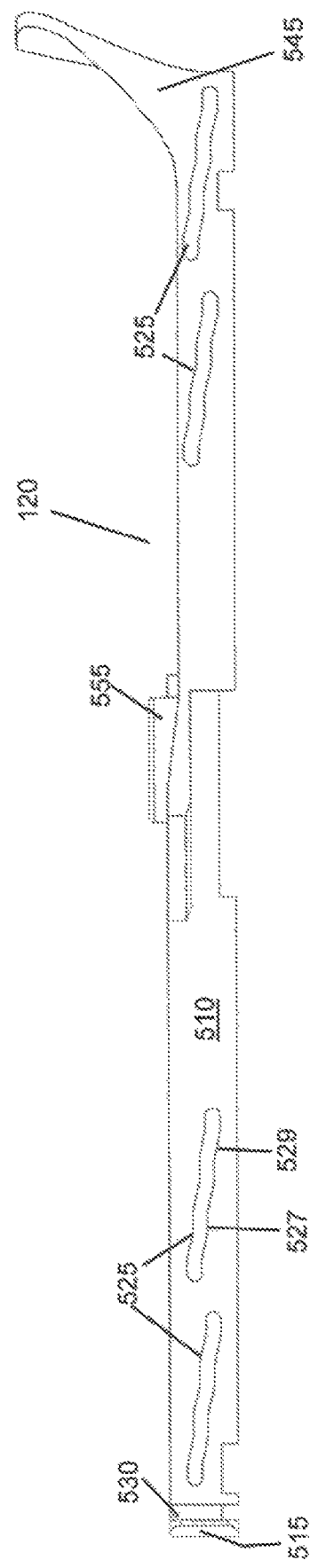
FIG. 5B
FIG. 5C

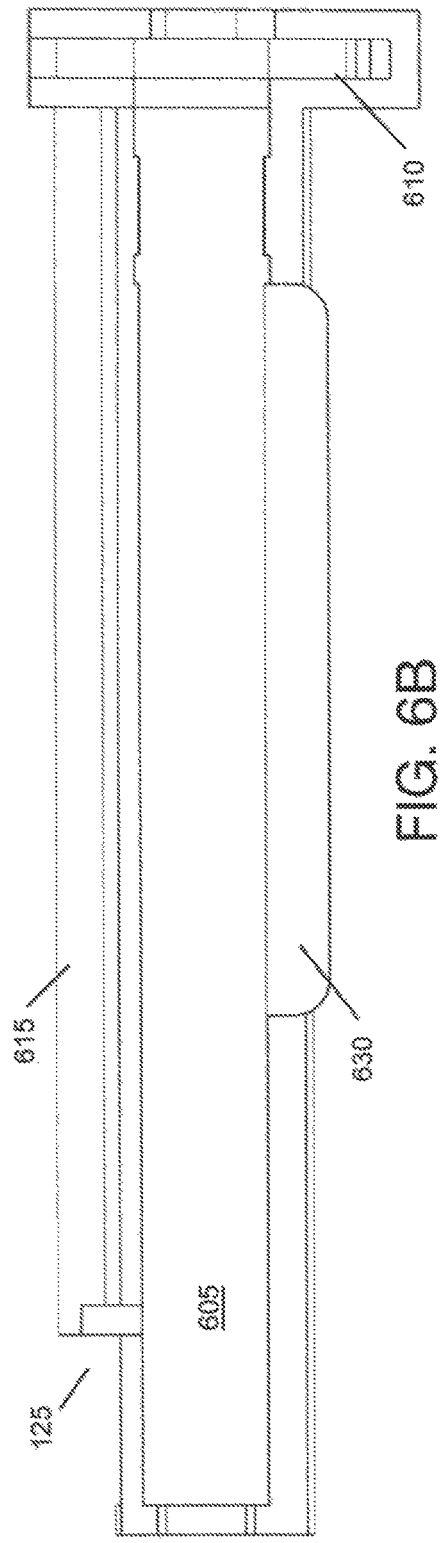
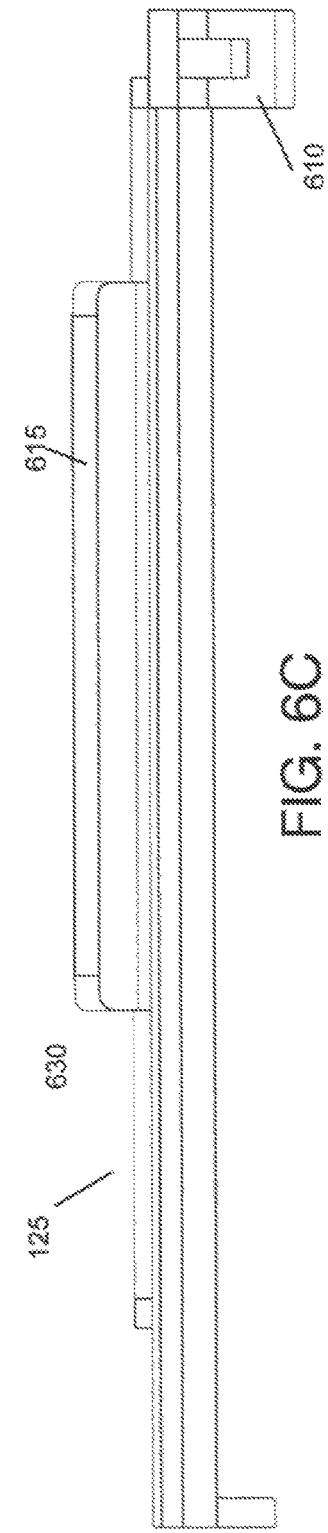
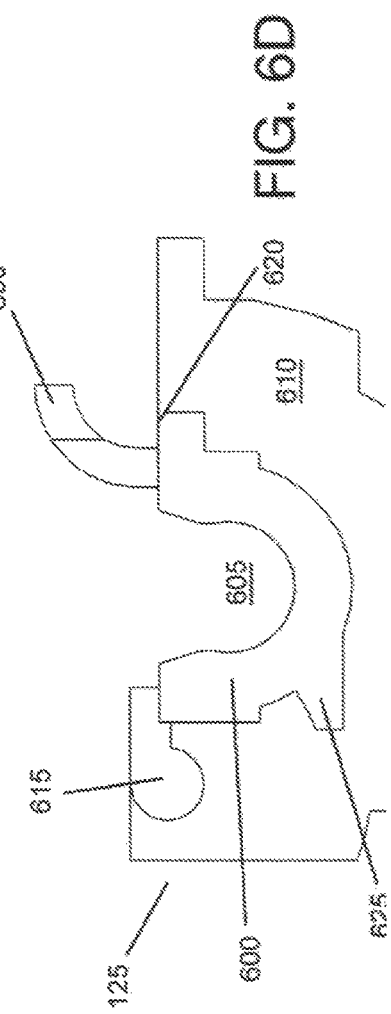
FIG. 6B
FIG. 6C
FIG. 6D

PARALLEL PATH PUNCTURE DEVICE GUIDE

This application is a national phase application under 35 U.S.C. § 371 of International Application No. PCT/US2020/053988, filed Oct. 2, 2020, which claims benefit of priority to U.S. Provisional Application No. 62/911,057, filed Oct. 4, 2019. The entire contents of each of the aforementioned applications is hereby incorporated by reference.

BACKGROUND

This invention relates to puncture device guidance devices for use with medical imaging instruments and more particularly to devices for guiding puncture devices to repeatable locations on a patient relative to a medical imaging instrument probe.

Imaging instruments, such as ultrasound probes, have revolutionized the manner in which many important medical procedures are performed. These medical instruments utilize imaging techniques to explore and assess the condition of human tissue and/or organs. As a result, diagnostic and therapeutic protocols have been developed that allow many highly successful and safe procedures to be performed with minimal disturbance to patients. For example, ultrasound probes have become an accepted modality for exploring endocavities, e.g., the digestive and reproductive tracts, of humans and animals in order to conduct routine examinations, as well as to identify evidence of tumors or other tissue regions of interest.

BRIEF DESCRIPTION OF THE DRAWINGS

FIGS. 1C and 1D are front views of the assembled needle guidance device of FIGS. 1A and 1B in raised and lowered configurations, respectively;

FIGS. 2A-2C are isometric, front, and left side views, respectively, of the probe holder member of FIGS. 1A and 1B;

FIGS. 3A-3E are isometric, top, bottom isometric, front, and left side views, respectively, of the body member of FIGS. 1A and 1B;

FIGS. 5A-5C are isometric, top, and front views, respectively, of the cradle member of FIGS. 1A and 1B;

FIGS. 6A-6D are isometric, top, front, and left side views, respectively, of the syringe cartridge member of FIGS. 1A and 1B.

DETAILED DESCRIPTION OF THE PREFERRED EMBODIMENTS

The following detailed description refers to the accompanying drawings. The same reference numbers in different drawings may identify the same or similar elements. Also, the following detailed description does not limit the invention.

Implementations described herein relate to guidance devices for facilitating the placement of a puncture device (e.g., a needle) at a defined position relative to an ultrasound probe. More specifically, the guidance devices described below include components that are adjustable to provide a number of parallel paths relative to each other and at different defined distances from the ultrasound probe. Accordingly, guidance devices consistent with the described embodiments allow for radial translation of the needle path without changing an angle of orientation relative to the ultrasound probe.

For example, in one implementation, the ultrasound probe may be a transrectal ultrasound probe and the guidance device may be configured to facilitate guidance of a hypodermic needle to administer medication at a location relative to the ultrasound probe. Consistent with embodiments described herein, the needle guidance device may be adjustable between a plurality of parallel paths while maintaining the angular orientation and axial relationship between the needle and the ultrasound probe.

Figure 1A:
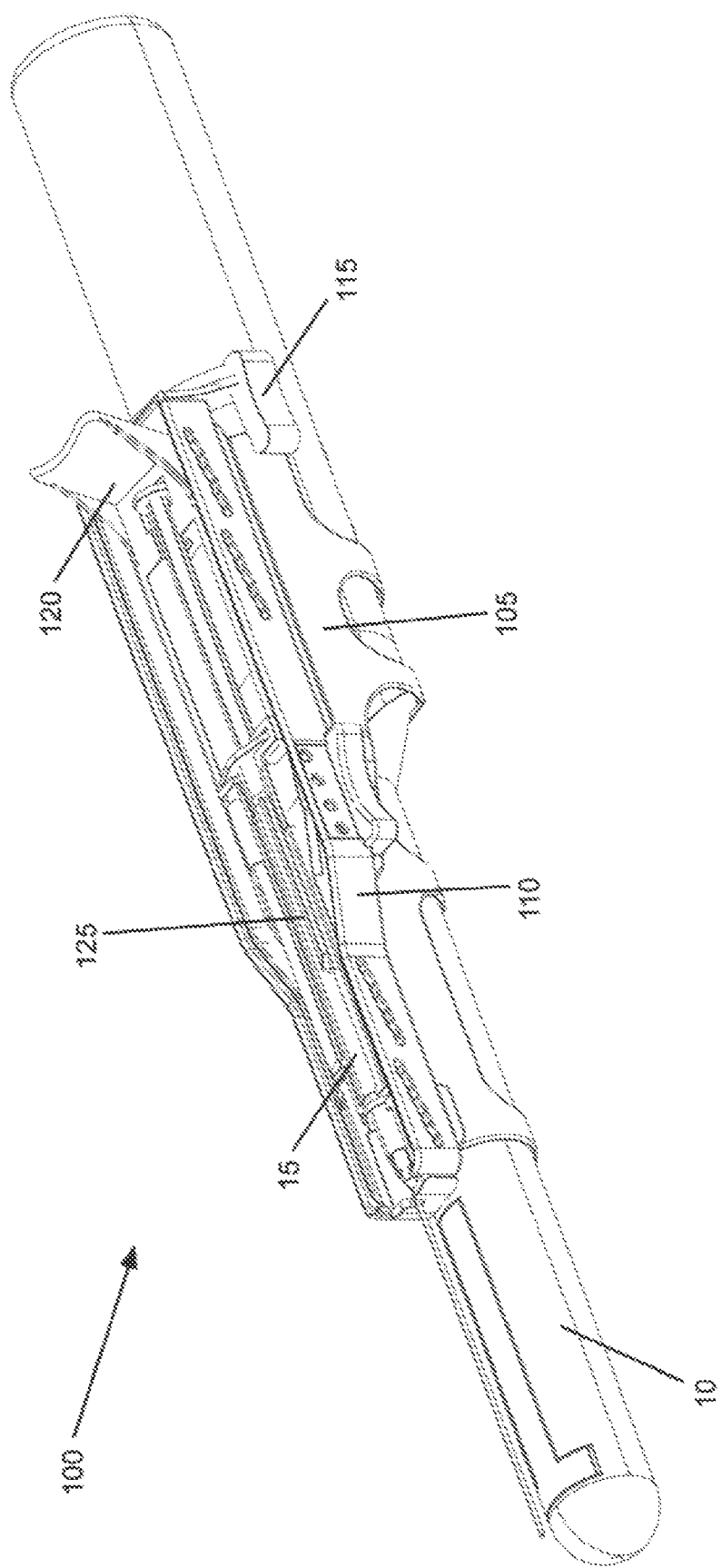
FIGS. 1A and 1B are isometric and exploded isometric views, respectively, illustrating one embodiment of a needle guidance device for use with an ultrasound probe, consistent with embodiments described herein.
Figure 1B:
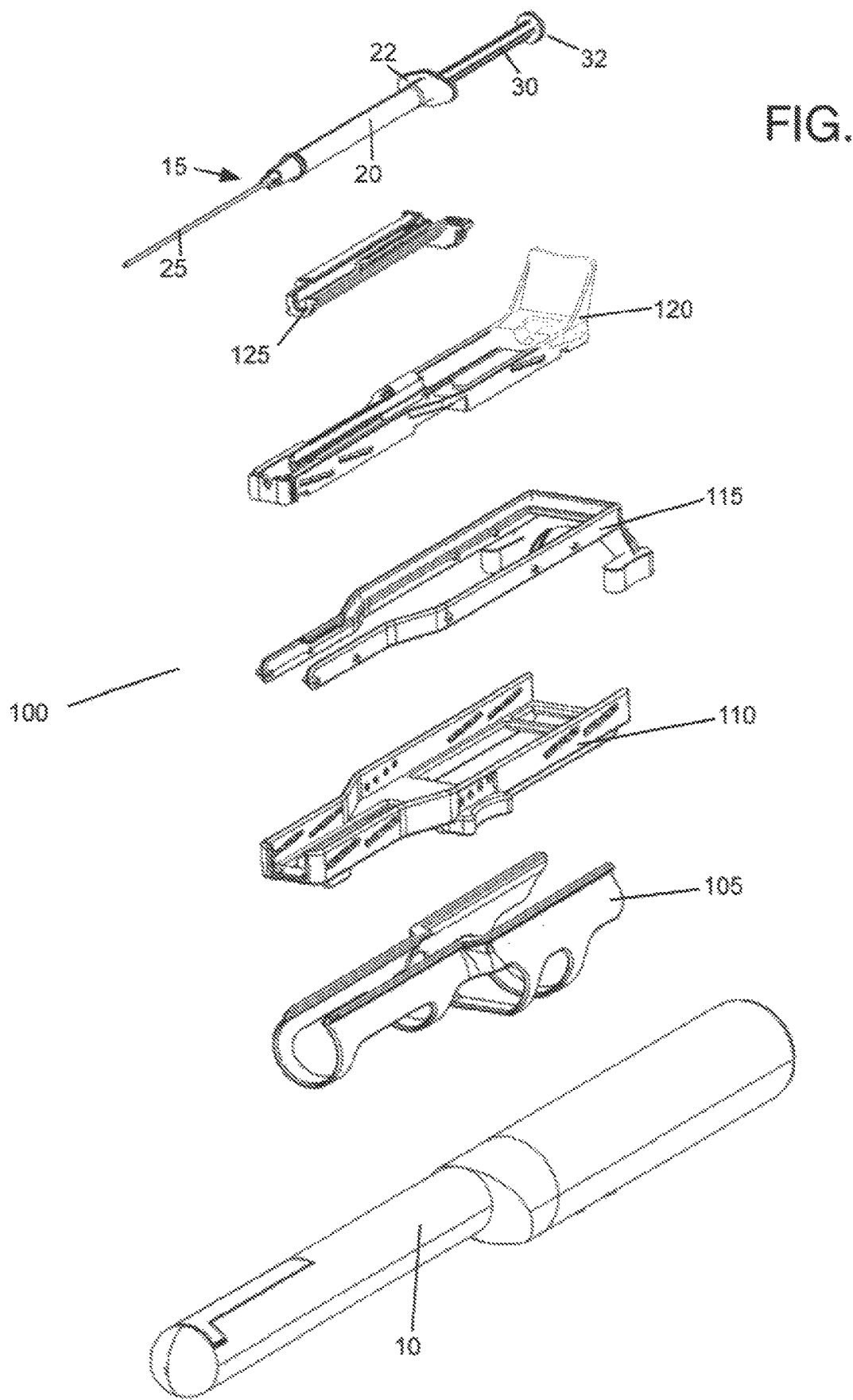

FIGS. 1A and 1B are isometric and exploded isometric views, respectively, illustrating one embodiment of a needle guidance device 100 for use with an ultrasound probe 10, consistent with embodiments described herein. As shown, needle guide device 100 includes a probe holder member 105, a body member 110, a slide member 115, a cradle member 120, and a syringe cartridge member 125.

In an assembled configuration and prior to administration, a hypodermic syringe 15 having a syringe barrel 20, a barrel flange 22, a needle 25, a plunger 30, and a plunger flange 32 may be received within needle guidance device 100 as described below. During use, syringe 15 is inserted into syringe cartridge member 125, which is then inserted into cradle member 120. Slide member 115 is moved to adjust the position of the needle 25 relative to the probe 10 and the needle is injected into the patient simultaneously with transrectal probe insertion. Via the cartridge member 125, the syringe barrel 20 is retracted within the cradle member 120 to release its contents during withdrawal from the patient. Syringe cartridge member 125 is then released from cradle member 120 and the used syringe is removed from syringe cartridge member 125.

FIGS. 2A-2C are isometric, front, and left side views, respectively, of probe holder member 105 of FIGS. 1A and 1B. Consistent with embodiments described herein, probe holder member 105 may include a generally tubular configuration sized and shaped to conform to an outer surface of ultrasound probe 10. As shown, an upper portion of holder member 105 includes attachment rails 200 that engage corresponding clip elements 315 projecting from a lower surface of body member 110, as shown in FIG. 3D and described in detail below. In one implementation, attachment rails 200 include opposingly oriented ribs or projections 210 that together form a planar upper surface 215 for supporting body member 110 thereon.

As shown in FIGS. 2A and 2C, in one embodiment, holder member 105 includes cutouts 217 for reducing the weight of holder member 105 and for allowing access to controls or ports positioned at various locations on ultrasound probe 10. Consistent with embodiments described herein, holder member 105 may be formed of a plastic or polymeric material and may be manufactured in any suitable manner, such as injection molding, extrusion molding, 3D printing, etc.

Although holder member 105 depicted in the figures illustrates a particular configuration, it should be understood that different configurations may be implemented based on the configuration of the ultrasound probe with which needle guide device 100 is to be used. Furthermore, although not depicted in the Figures, in use, a sterile sheath or other cover may be place on or over ultrasound probe 10 prior to attachment of ultrasound probe 10.

Figure 3A:
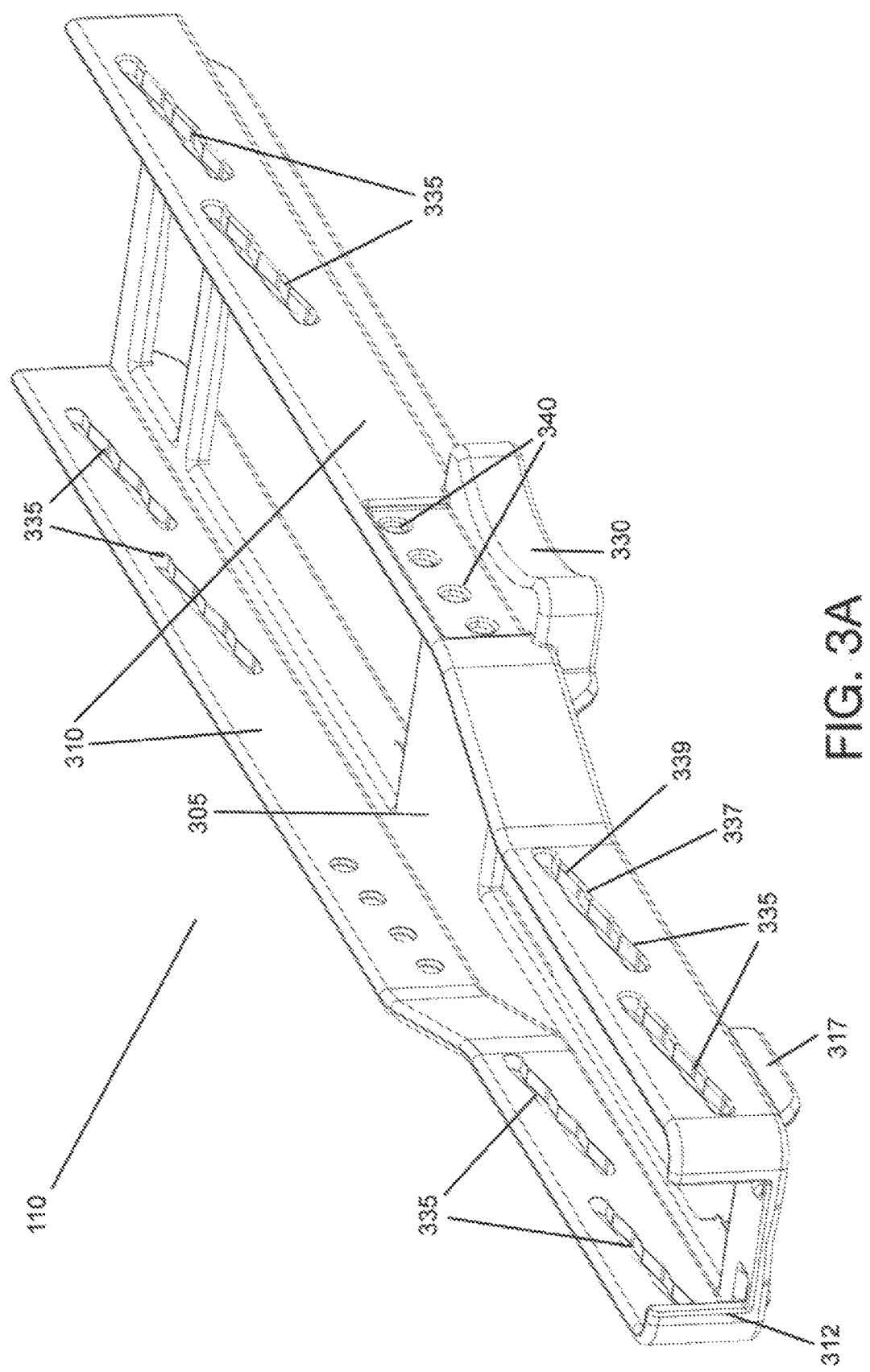
Figure 3D:
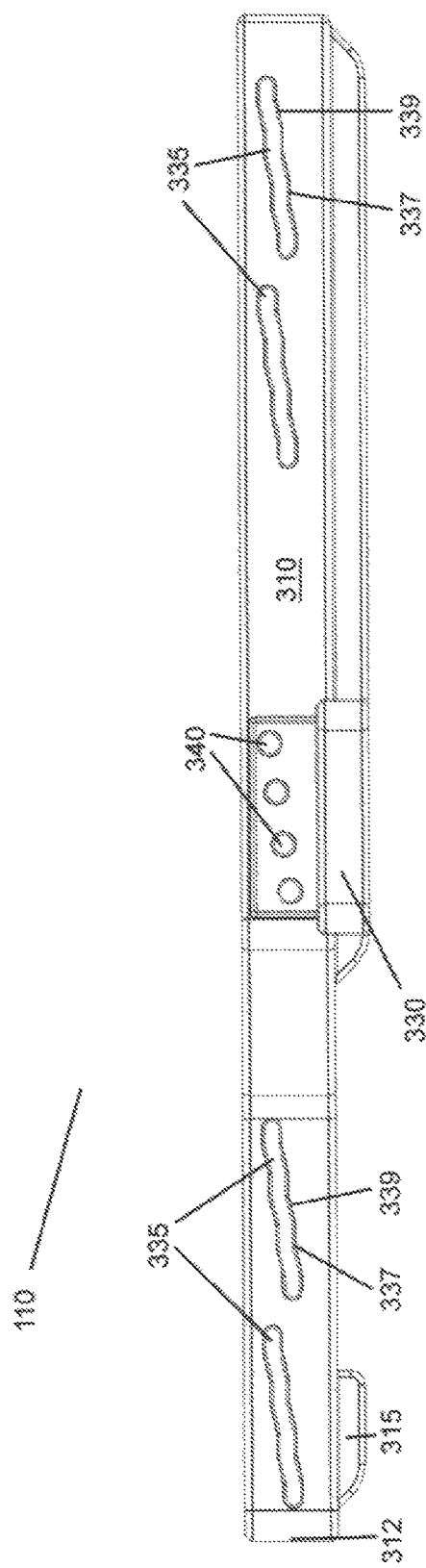

FIGS. 3A-3E are isometric, top, bottom isometric, front, and left side views, respectively, of body member 110 of FIGS. 1A and 1B. As shown, body member 110 includes a generally frame-like structure having a bottom portion 305, side rails 310, and a front rail 312. Side rails 310 and front rail 312 project upwardly from bottom portion 305 around a periphery thereof. Together, bottom portion 305, side rails 310, and front rail 312 are configured to receive slide member 115 and cradle member 120, as described below. As shown in FIGS. 3C-3D, body member 110 may further include a plurality of clip elements 315 and positioning pins 325. Clip elements 315 are spaced to engage attachment rail 200 in holder member 105, as described above. In particular, each clip element 315 may include a downward projection 317, which projects downwardly from bottom portion 305 and barb member 319, which projects inwardly from the downward projection 317. Positioning pins 325 may project downwardly from bottom portion 305 and may engage an upper surface of ultrasound probe 10 to allow for longitudinal positioning of body member relative to ultrasound probe 10.

Regarding clip elements 315, the dimensions and locations of downward projection 317 and barb members 319 relative to bottom portion 305 of body member 110 correspond with attachment rail 200, such that during assembly, clip elements 315 frictionally engage attachment rail 200. More specifically, in one implementation, during assembly, a downward force is placed on body member 110, which causes barb members 319 to engage a top of attachment rails 200. Continued downward force, causes angled lower surfaces on barb members 319 to slidingly engage attachment rails 200 thus causing downward projections 317 to splay outwardly, allowing barb members 319 to slide around and fully engage attachment rails 200. In other implementations, clip elements 315 may not include barb members 319, but may rather include non-angled inward projections. In such an embodiment, body member 110 may be longitudinally slid onto attachment rails 200 during assembly.

As shown in FIGS. 3A, 3B, and 3D, body member 110 may further include hand engagement portions 330, which project outwardly from a lower portion of side rails 310 and centrally positioned downward projections 317. Hand engagement portions 330 may provide users with a surface to affect assembly (e.g., clipping) of body member 110 to holder member 105.

As shown in FIGS. 3A, 3C, and 3D, side rails 315 may include a plurality of path adjustment channels 335 and path selection apertures 340. In the illustrated embodiment, body member 110 includes four opposing pairs of path adjustment channels 335 and four opposing pairs of path selection apertures 340. In other implementations more or fewer path adjustment channels 335 and/or path selection apertures 340 may be used. Furthermore, although pairs of channels 335 and apertures 340 are illustrated, in some implementations, channel(s) 335 and/or aperture(s) 340 may be provided on only one side or on alternate sides of body member 110.

Consistent with embodiments described herein, each of path adjustment channels 335 forms a generally angled channel having a plurality of planar portions 337 and angled portions 339 corresponding to a number of possible path positions. In the illustrated embodiment, each path adjustment channel 335 includes four planar portions 337 and three angled portions 339 provided between each planar portion 337. Although not restricted herein, in one implementation, a vertical distance between a bottom of a first planar portion 337 (shown in FIG. 3D) and fourth planar portion 337 (also shown in FIG. 3D) is in the range of 0.5 to 1.5 centimeters (cm). In the same exemplary embodiment, the longitudinal distance between the center of first planar portion 337 and the center of fourth planar portion 337 is in the range of 5 to 12 cm. As described below, each of path adjustment channels 335 is configured to receive corresponding portion(s) of slide member 115 to thus restrict the movement of slide member to those positions defined by path adjustment channels 335.

Path selection apertures 340 are spaced and positioned to correspond to planar portions 337 in path adjustment channels 335. As described below, one of path selection apertures 337 is configured to receive a corresponding portion of slide member 115 to positively retain slide member 115 in the positioned defined by one of planar portions 337 and prevents inadvertent movement along path adjustment channel(s) 335 during use.

Figure 3E:
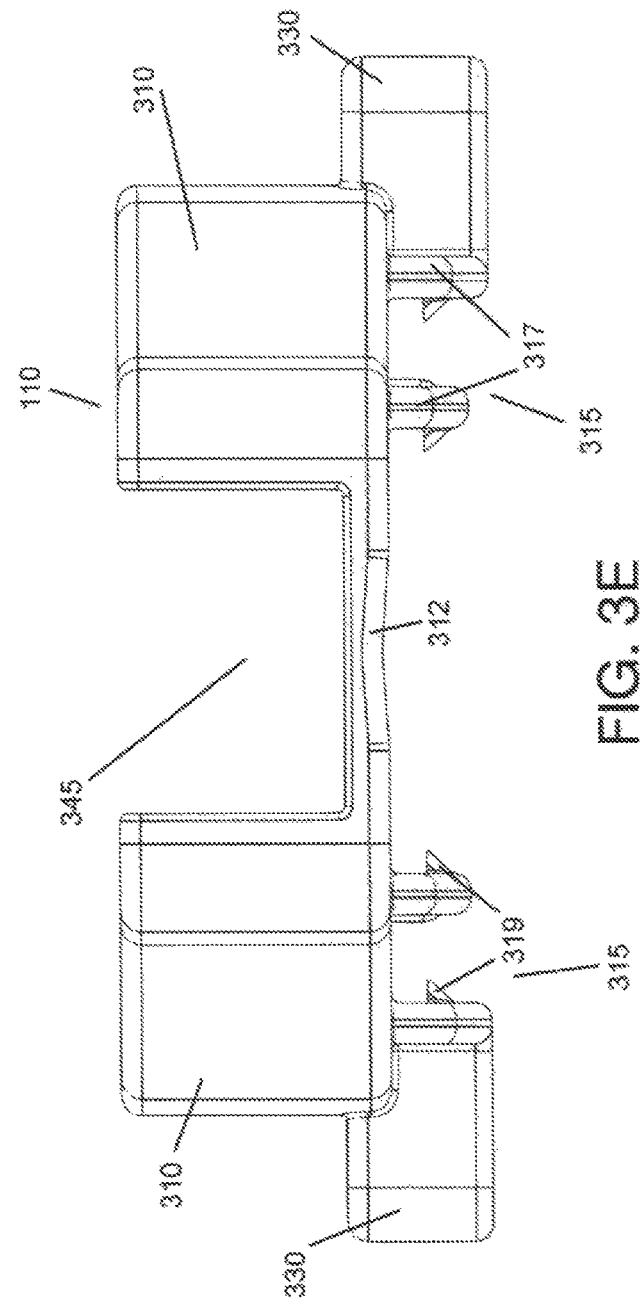

As shown in FIG. 3E, front rail 312 may include a central opening 345 aligned with a longitudinal axis of body member 110 and configured to engage a portion of cradle member 120 in the manner described below.

Figure 4A:
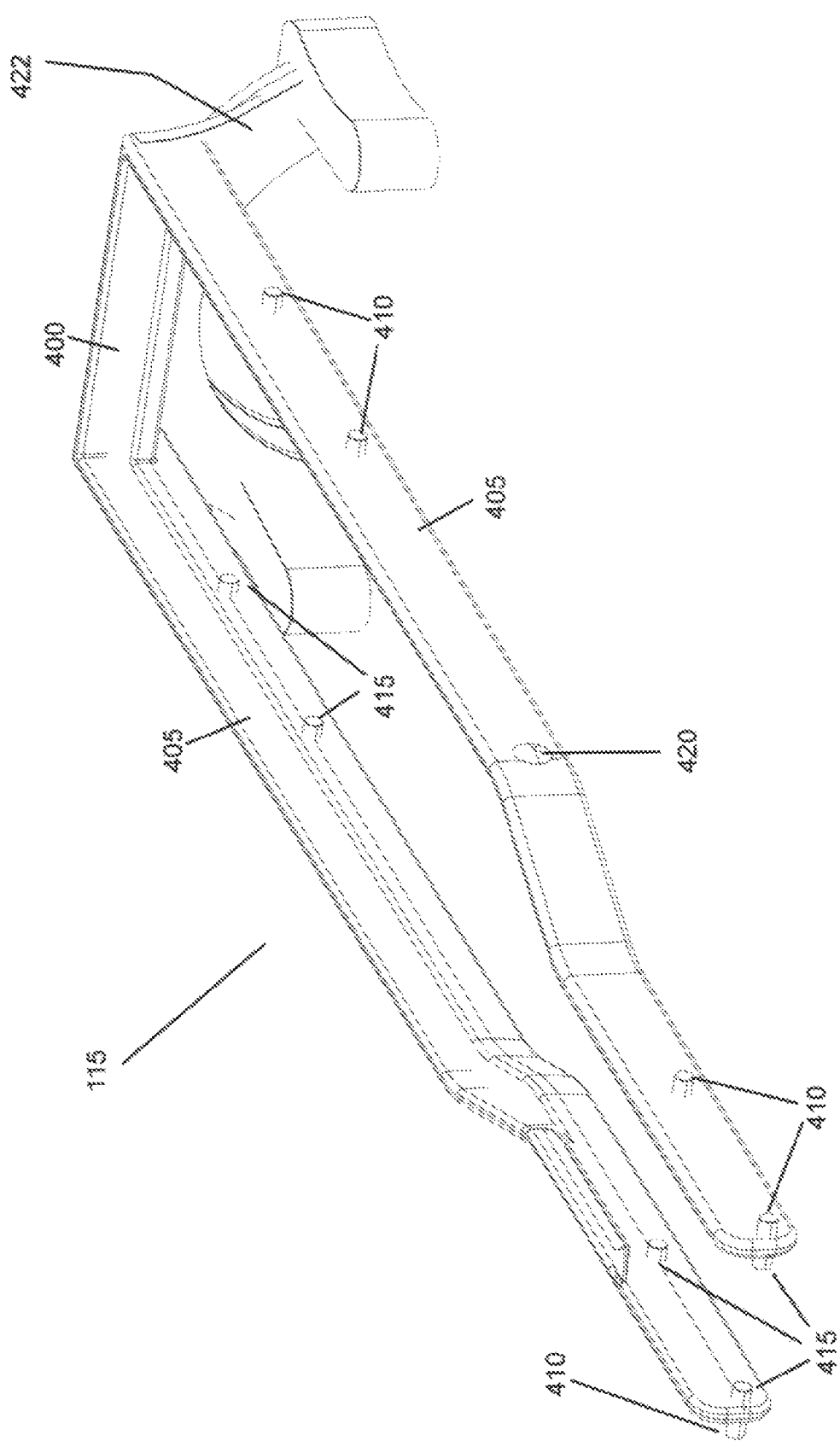
FIGS. 4A-4C are isometric, top, and front views, respectively, of the slide member of FIGS. 1A and 1B.
Figure 4B:
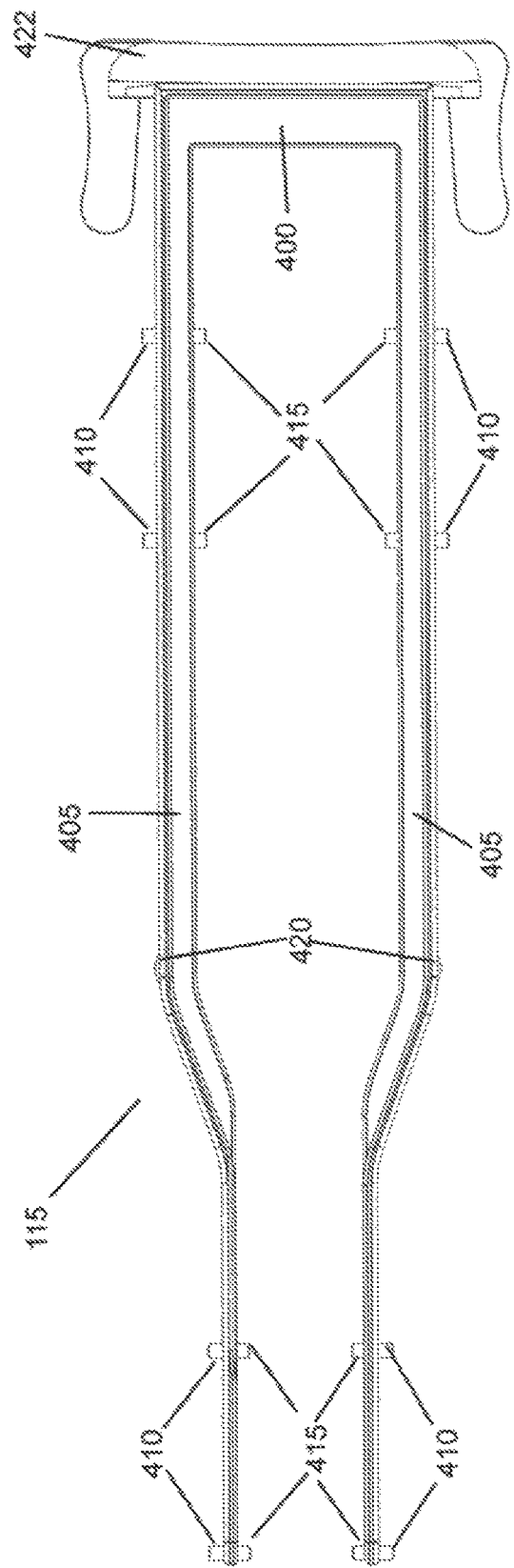
Figure 4C:
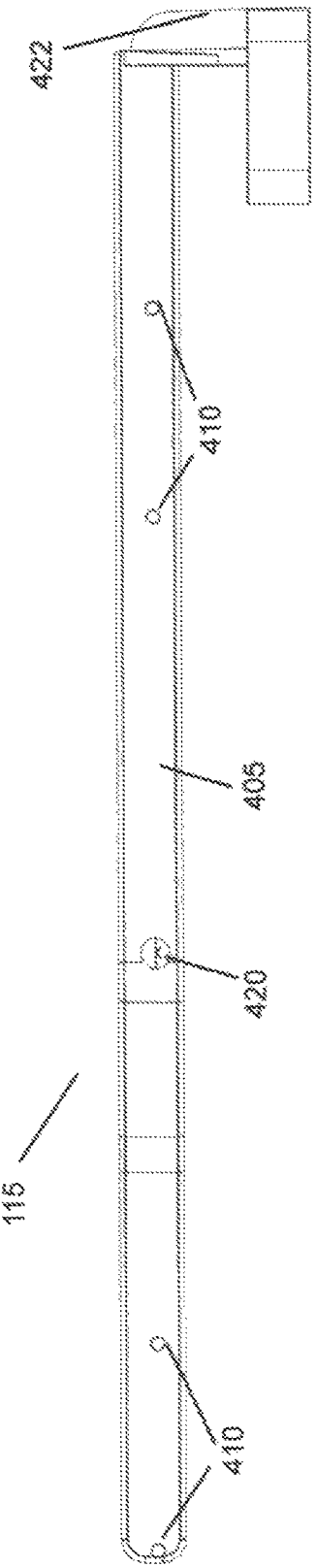

FIGS. 4A-4C are isometric, top, and front views, respectively, of slide member of 115. Consistent with embodiments described herein slide member 115 includes a generally C-shaped configuration having an end 400 and side rails 405 and. Each of side rails 405 are sized substantially similarly to an inside dimension of body member side rails 315, such that upon assembly, side rails 405 of slide member 115 may engage the inside surfaces of body member side rails 315.

As shown in FIGS. 4A and 4B, side rails 405 of slide member 115 include a plurality of outer path selection pins 410 and inner path selection pins 415. Each of outer path selection pins 410 projects outwardly from side rails 405 and is sized and positioned for captured receipt within path adjustment channels 335 during assembly. Similarly, each of inner path selection pins 415 projects inwardly from side rails 405 and is sized and positioned for captured receipt within path adjustment channels 525 of cradle member 120 during assembly. Additional details of cradle 120 are described below.

Side rails 405 of slide member 115 further includes one or more path retaining detents 420. As shown in FIG. 4A, path retaining detent 420 may be positioned and sized to engage one of path selection apertures 340 in side rails 315 of body member 110. As described above, during use, the engagement of outer path selection pins 410 with path adjustment channels 335 may define the movement of slide member 115 relative to body member 110. Once outer path selection pins 410 are positioned on a particular planar portion 337 in path adjustment channels 335, path retaining detent 420 on side rail 405 of slide member 115 is engaged in a corresponding path selection aperture 340, thus retaining slide member 115 in the position.

End 400 of slide member 115 includes a handle portion 422. As shown in FIG. 4A, in one implementation, handle portion 422 includes a configuration that is complementary to a portion of ultrasound probe 10, such that a user may grasp or engage both probe 10 and handle portion 420 simultaneously. During use, an operator may affect longitudinal movement of slide member 115 by engaging handle portion 420 and moving slide member 115 forward and/or backward, as defined by path adjustment channels 335 and outer path selection pins 410.

Figure 5A:
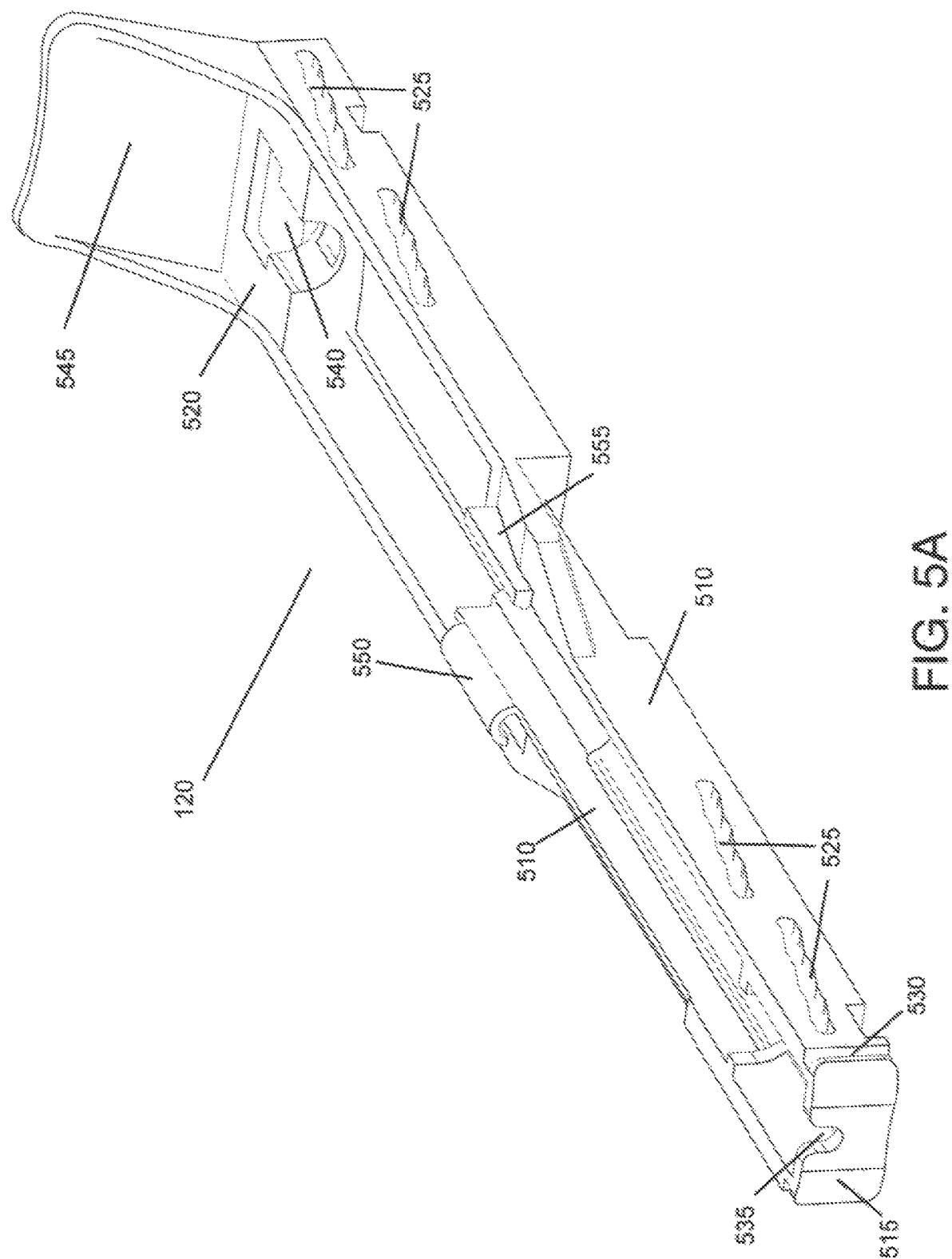
Figure 6A:
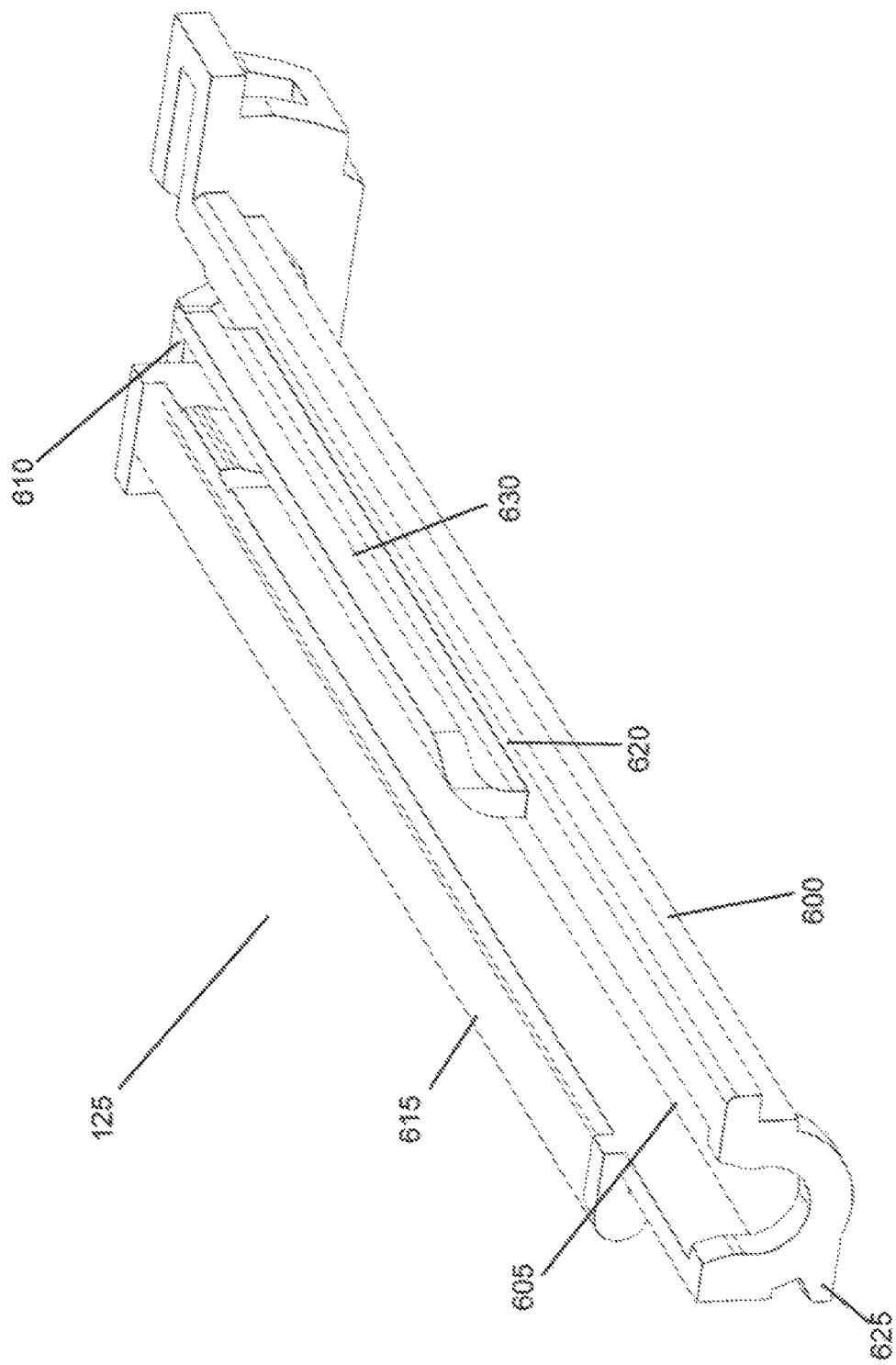

FIGS. 5A-5C are isometric, top, and front views, respectively, of cradle member 120. As shown, cradle member 120 includes a generally frame-like structure having a bottom portion 505, central cavity 507, side walls 510, front wall 515, and rear portion 520. Side wall 510, front wall 515, and rear portion 520 project upwardly from bottom portion 505 around a periphery thereof to form a generally box-like structure. Central cavity 507 of cradle member 120 is sized to receive syringe cartridge member 125 in the manner described below. Each of side walls 510 are sized substantially similarly to an inside dimension of slide member 115, such that upon assembly, side walls 510 engage the inside surfaces of side rails 405 of slide member 115. Furthermore, as described below in relation to FIG. 5C, cradle member 120 is configured to be longitudinally fixed with respect to body member 110 upon assembly, while retaining the capacity to move vertically with respect to body member 110.

As shown in FIGS. 5A and 5C, side walls 510 of cradle member 120 include a plurality of path adjustment channels 525. In the illustrated embodiment, cradle member 120 includes four opposing pairs of path adjustment channels 525 (although only one side of each pair are depicted in the Figures). In other implementations more or fewer path adjustment channels 525 may be used. Furthermore, although pairs of channels 525 are illustrated, in some implementations, channel(s) 525 may be provided on only one side or on alternate sides of cradle member 120.

Consistent with embodiments described herein, and similar to path adjustment channels 335 in body member 110, each of path adjustment channels 525 in cradle member 120 also forms a generally angled channel having a plurality of planar portions 527 and angled portions 529 corresponding a number of possible path positions. In the illustrated embodiment, each path adjustment channel 525 includes four planar portions 527 and three angled portions 529 provided between each planar portion 527.

In contrast to path adjustment channels 335 in body member 110, path adjustment channels 525 in cradle member 120 are oriented in an opposite manner. That is, as shown in FIG. 1A, whereas path adjustment channels 335 in body member 110 are oriented generally upwardly in a front to back direction of needle guidance device 100, path adjustment channels 525 in cradle member 120 are oriented generally downwardly. Aside from the reverse orientation, path adjustment channels 525 otherwise conform to path adjust channels 335 in terms of spacing, height, angle, etc. Path adjustment channels 525 in cradle member 120 are further configured to receive inner path selection pins 415 in slide member 115, such that longitudinal movement of slide member 115 relative to cradle member 120 causes cradle member 120 to move upwardly or downwardly, as inner path selection pins 415 travel within path adjustment channels 525.

By virtue of the opposing nature of path adjustment channels 335 in body member 110 and path adjustment channels 525 in cradle member 120, as slide member 115 is moved longitudinally forward or backward, cradle member 120 is translated vertically (also referred to as radially) relative to body member 110, while maintaining parallel orientations with respect to each other. For example, as shown in FIGS. 1C and 1D, as the slide member 115 moves rearwardly (e.g., from the position shown in FIG. 1C to the position shown in FIG. 1D), outer path selection pins 410 in slide member 115 move rearwardly and upwardly within path adjustment channels 335 in body member 110, while simultaneously inner path selection pins 415 in slide member 115 move rearwardly and downwardly within path adjustment channels 525 in cradle member 120.

As shown in FIGS. 5A-5C, front wall 515 of cradle member 120 includes vertical notches 530 and needle path opening 535. Vertical notches 530 are formed on opposing sides of front wall 515 between front wall 515 and side walls 510 and are sized to receive central opening 345 in front rail 312 of body member HO. Such a configuration causes cradle member 120 to be fixed longitudinally with respect to body member 110, while retaining freedom of movement in a vertical direction. As shown in FIG. 1A, needle path opening 535 provides on opening through front wall 515 through which needle 25 may pass during use. Consistent with implementations described herein, needle path opening 535 is configured such that needle 25 does not contact cradle 120 in any manner during use. In this way, cradle 120 may be used throughout a patient procedure without risk of contamination.

As shown in FIG. 5A, consistent with embodiments described herein, rear portion 520 of cradle member 120 includes a plunger capture cavity 540 and a syringe retraction support 545. Plunger capture cavity 540 is formed as a recess within cradle member 120 sized to receive and longitudinally retain the flange and a portion of the shaft of syringe plunger 30, as shown in FIG. 1A. Syringe retraction support 545 provides a clear base for users to grasp when retracting syringe barrel 20 toward the plunger flange, as described in further detail below.

As shown in FIGS. 5A and 5B, cradle member 120 further includes a syringe cartridge ejector hinge portion 550 and a syringe cartridge retaining element 555. As described in additional detail below with respect to syringe cartridge member 125, syringe cartridge ejector hinge portion 550 includes a tubular projection that extends outwardly from an upper surface of cradle member 120. During use, a corresponding portion of syringe cartridge member 125 is rotatably and longitudinally slidably received within syringe cartridge ejector hinge portion 550. Syringe cartridge retaining element 555 projects slightly inwardly from side wall 510 opposite syringe cartridge ejector hinge portion 550 so as to slidably retain syringe cartridge member 125 upon installation.

FIGS. 6A-6D are isometric, top, front, and left side views, respectively, of syringe cartridge member 125. As shown, syringe cartridge member 125 includes a body portion 600, a central cavity 605, a barrel flange portion 610, a hinge portion 615, a retaining portion 620, a stop portion 625, and a release member 630. Syringe cartridge member 125 may be formed from a semi-rigid material, such as a plastic or polymer. In general, syringe cartridge member 125 supports hypodermic syringe 15 and is sized for reception within central cavity 507 of cradle member 120. Body portion 600 of syringe cartridge member 125 includes a generally trough-shaped configuration having an extended U-shape, with central cavity 605 sized and shaped to accommodate barrel 20 for syringe 15 to be used with the device 100.

Barrel flange portion 610 is located at a rearward end of syringe cartridge member 125 and includes a cavity perpendicular to central cavity 605 and sized to receive the barrel flange 22 of hypodermic syringe 15. Hinge portion 615 includes a substantially cylindrical projection that extends outwardly away from one side of body portion 600. Retaining portion 620 includes an upper shoulder element of a side of body portion 600 opposite to hinge portion 615.

Stop portion 625 of syringe cartridge member 125 includes an element that projects from a lower, forward portion of body portion 600 and is configured to engage an inside portion of central cavity 507 of cradle member 115 when syringe cartridge member 125 is fully seated within cradle member 115.

Release member 630 of syringe cartridge member 125 includes a vertical projection positioned adjacent to retaining portion 620. In the embodiment of FIG. 6A-6D, release member includes a curved or partial tubular configuration. However, in other implementations, release member 630 may be configured to include a straight or angled configuration. Upon completion of a procedure, release member 630 may be deflected inwardly, causing retaining portion 620 to release from syringe cartridge retaining element 555 in cradle member 115, thereby allowing cartridge member 125 to rotate upwardly within hinge portion 550 of cradle member 115.

Prior to use of device 100, hinge portion 615 of syringe cartridge member 125 is inserted into syringe cartridge ejector hinge portion 550 of cradle member 120. Hypodermic syringe barrel 20 is then inserted into central cavity 605 and barrel flange 22 into barrel flange portion 610. Hinge portion 615 of syringe cartridge member 125 is then rotated (e.g., clockwise) within syringe cartridge ejector hinge portion 550 until stop portion 625 engages an inside of central cavity 507.

Figure 7A:
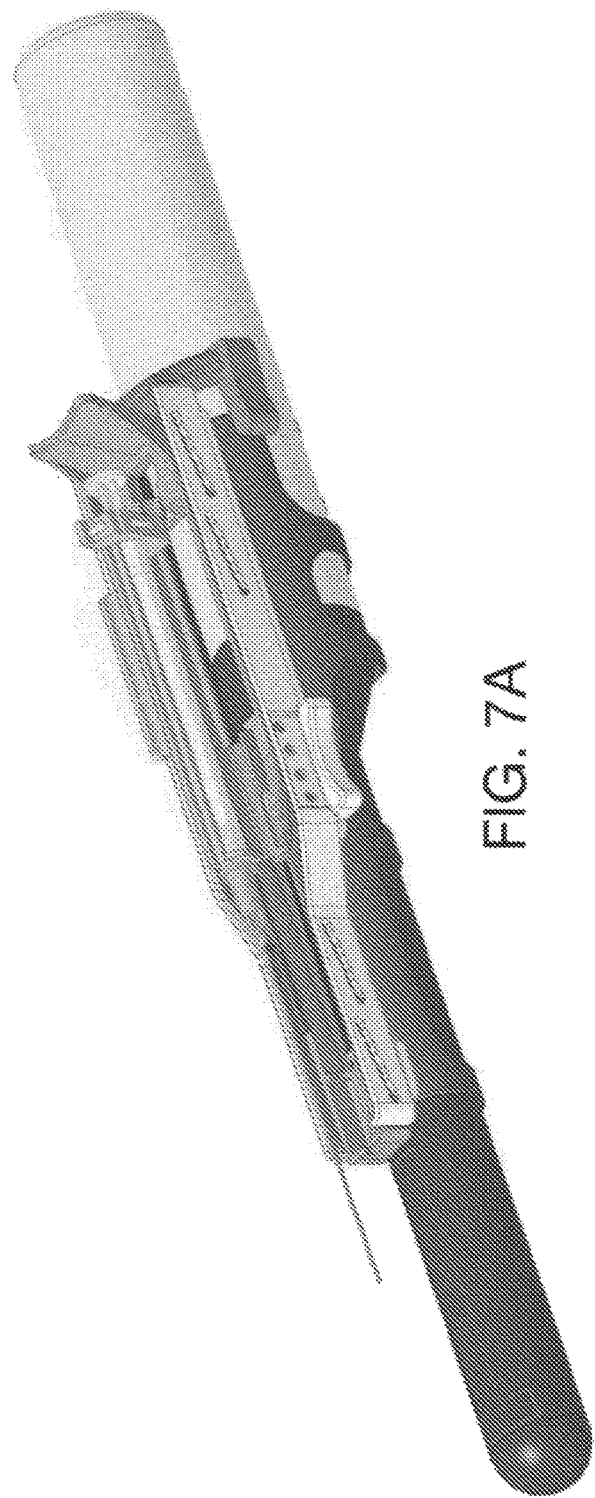
FIGS. 7A and 7B are isometric illustrations of the ejector body mechanisms during ejection of the hypodermic syringe from the needle guidance device of FIGS. 1A and 1B.
Figure 7B:
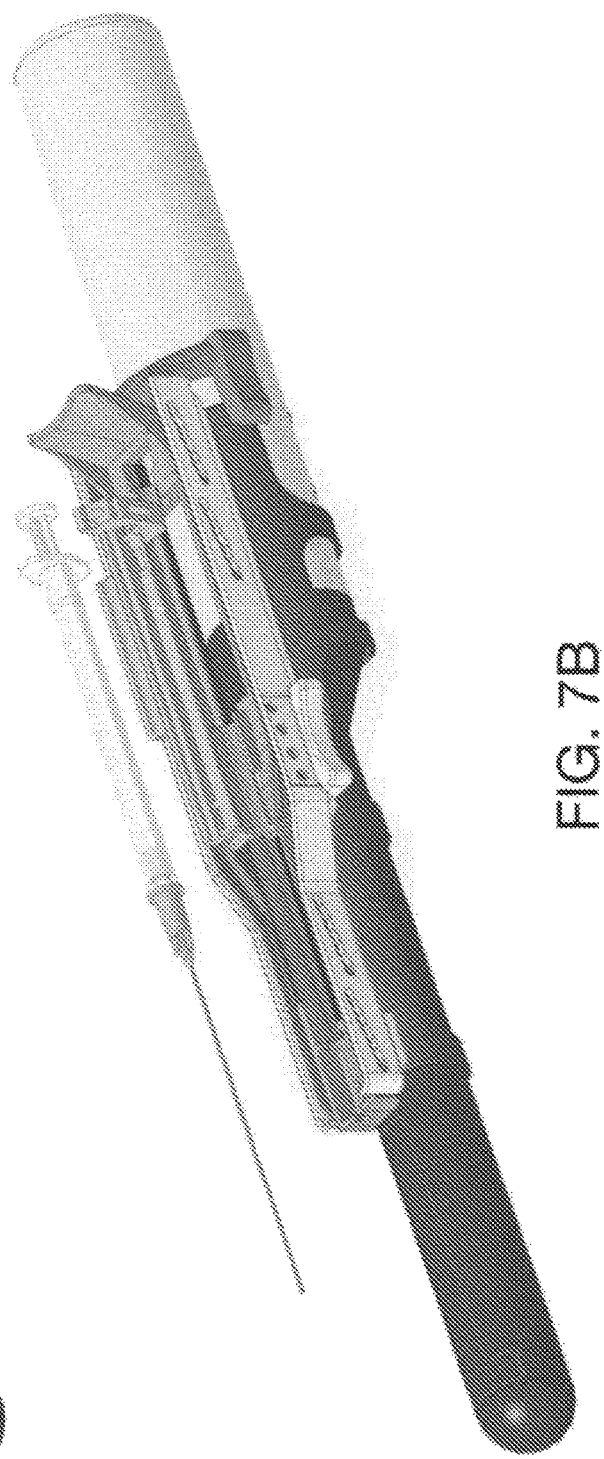

As described above, during use, slide member 115 is moved axially and radially to a desired position corresponding to a selected needle path. Once positioned, the transducer probe 10 and needle 25 are inserted into the patient, with the ultrasound image being used to guide the depth. Once properly positioned, the operator retracts the syringe by pulling barrel flange portion 610 towards syringe retraction support 545 of cradle member 120. Once fully retracted, the operator may deflect release member 630, which causes retaining portion 620 to release from syringe cartridge retaining element 555. The user may then rotate syringe cartridge member 125 in a counterclockwise manner, to effect removal of the used syringe 15. The removal process is depicted in FIGS. 7A and 7B.

The foregoing description of exemplary implementations provides illustration and description but is not intended to be exhaustive or to limit the embodiments described herein to the precise form disclosed. Modifications and variations are possible in light of the above teachings or may be acquired from practice of the embodiments.

Although the invention has been described in detail above, it is expressly understood that it will be apparent to persons skilled in the relevant art that the invention may be modified without departing from the spirit of the invention. Various changes of form, design, or arrangement may be made to the invention without departing from the spirit and scope of the invention. Therefore, the above-mentioned description is to be considered exemplary, rather than limiting, and the true scope of the invention is that defined in the following claims.

No element, act, or instruction used in the description of the present application should be construed as critical or essential to the invention unless explicitly described as such. Also, as used herein, the article "a" is intended to include one or more items. Further, the phrase "based on" is intended to mean "based, at least in part, on" unless explicitly stated otherwise.

Use of ordinal terms such as "first," "second," "third," etc., in the claims to modify a claim element does not by itself connote any priority, precedence, or order of one claim element over another, the temporal order in which acts of a method are performed, the temporal order in which instructions executed by a device are performed, etc., but are used merely as labels to distinguish one claim element having a certain name from another element having a same name (but for use of the ordinal term) to distinguish the claim elements.

What is claimed is:

1. A puncture device guide, comprising:
    a body member configured to fixedly attach to an ultrasound probe;
    a slide member slidingly received within the body member; and
    a cradle member slidingly received within the slide member and longitudinally fixed relative to the body member,
    wherein the cradle member is configured to receive a puncture device therein, and
    wherein longitudinal movement of the slide member causes radial movement of the cradle member relative to the body member;
    wherein the body member comprises at least one first path adjustment channel that defines a range of radial and longitudinal movement for the slide member,
    wherein the cradle member comprises at least one second path adjustment channel configured oppositely to the at least first path adjustment channel, and
    wherein the slide member is configured to slidingly engage each of the at least one first path adjustment channel and the at least one second path adjustment channel, wherein the slide member includes at least one first path selection pin configured to be retained within the at least one first path adjustment channel and at least one second path selection pin configured to be retained within the at least one second path adjustment channel,
    wherein the slide member comprises side rails,
    wherein a first side of the side rails is configured to slidingly engage the body member and a second side of the side rails is configured to slidingly engage the cradle member,
    wherein the at least one first path selection pin is positioned on the first side of the side rails, and
    wherein the at least one second path selection pin is positioned on the second side of the side rails.

2. The puncture device guide of claim 1, wherein the at least one first path adjustment channel is angled radially relative to the body member in a first direction and wherein the at least one second path adjustment channel is angled radially relative to the body member in a second direction opposite to the first direction.

3. The puncture device guide of claim 2, wherein each of the at least one first path adjustment channel and the at least one second path adjustment channel comprise one or more angled portions and one or more planar portions, wherein the positions of the one or more planar portions correspond to a plurality of defined path positions.

4. The puncture device guide of claim 1, wherein the slide member comprises a path retaining element configured to releasably fix the slide member to the body member.

5. The puncture device guide of claim 4, wherein the body member comprises a plurality of path selection apertures, and
    wherein the path retaining element is configured to be received in a respective one of the plurality of path selection apertures to define a selected puncture device path position.

6. The puncture device guide of claim 1,
    wherein the body member comprises side rails, and
    wherein the cradle member comprises at least one vertical notch configured to receive a portion of the side rails of the body member, such that longitudinal movement of the cradle member relative to the body member is prevented, while the radial movement of the cradle member relative to the body member is allowed.

7. The puncture device guide of claim 1, further comprising:
 a puncture device cartridge member for receiving at least a portion of the puncture device therein,
 wherein the cartridge member is slidingly received within the cradle member and moveable between a first longitudinal position and a second longitudinal position within the cradle member.

8. The puncture device guide of claim 7,
 wherein each of the cartridge member and the cradle member comprise mating hinge portions configured to allow the cartridge member to be rotated between a first position in which the puncture device may be inserted or removed from the cartridge member to a second position in which the cartridge member is inserted within the cradle member.

9. The puncture device guide of claim 8, wherein the cartridge member includes a release member, deflection of which by a user causes the cartridge member to rotate between the first and second positions.

10. The puncture device guide of claim 7, wherein the puncture device comprises a syringe and wherein the cradle member is configured to retain a plunger portion of the syringe, such that sliding movement of the cartridge member relative to the cradle member causes depressing of the syringe.

11. The puncture device guide of claim 1, further comprising:
 a probe holder member configured to releasably receive the ultrasound probe therein,
 wherein the body member is secured to the probe holder member.

12. The puncture device guide of claim 11, wherein the probe holder member comprises at least one attachment rail, and
 wherein the body member comprises one or more clip elements for releasable attachment to the at least one attachment rail.

* * * * *